United States Patent [19]
Jacobi

[11] Patent Number: 5,188,595
[45] Date of Patent: Feb. 23, 1993

[54] METHOD FOR ENHANCED RETENTION OF BALLOON CATHETER IN BODY CAVITY

[75] Inventor: Roger P. Jacobi, San Jose, Calif.

[73] Assignee: Laserscope, San Jose, Calif.

[21] Appl. No.: 722,339

[22] Filed: Jun. 28, 1991

[51] Int. Cl.$^5$ .................. A61M 31/00; A61M 5/32
[52] U.S. Cl. ............................ 604/53; 604/176
[58] Field of Search ..................... 604/51–54, 604/96, 101, 102, 174, 176

[56] References Cited

U.S. PATENT DOCUMENTS

| | | | |
|---|---|---|---|
| 2,701,559 | 2/1955 | Cooper | 128/749 |
| 3,417,744 | 12/1968 | Mishkin et al. | 604/101 X |
| 3,765,413 | 10/1973 | Lepar | 604/176 |
| 4,180,076 | 12/1979 | Betancourt | 604/101 |
| 4,423,725 | 1/1984 | Baran et al. | 604/101 X |
| 4,447,227 | 5/1984 | Kotsanis | 604/95 |
| 4,781,677 | 11/1988 | Wilcox | 604/28 |
| 4,930,496 | 6/1990 | Bosley, Jr. | 128/24 A |

*Primary Examiner*—John D. Yasko
*Assistant Examiner*—Adam J. Cermak
*Attorney, Agent, or Firm*—Kenneth D'Alessandro

[57] ABSTRACT

A retention catheter comprises a length of flexible tubing having first and second ends, including first, second, and third axial lumens running therethrough. The first lumen includes first and second apertures located proximately to the first and second ends of said tubing, and is adapted to conduct fluid therethrough to or from a body cavity or vessel through the catheter. First and second inflatable balloons are circumferentially disposed about the outside of the tubing located proximate to a first end thereof. The first and second balloons are separated by a selected distance, and communicate with the second lumen through the tubing. The third lumen through the tubing terminates at a first end in a first aperture located on the outer wall of the tubing between the first and second balloons and at a second end in a vacuum aperture located proximate to the second end of the tubing opposite to the balloon end. The catheter is secured by a process which includes the steps of first inserting the catheter into a body cavity or vessel, inflating the balloons, and pulling a vacuum in the volume defined between the balloons and the inside of the wall of vessel or body cavity.

8 Claims, 2 Drawing Sheets

METHOD FOR ENHANCED RETENTION OF BALLOON CATHETER IN BODY CAVITY

BACKGROUND OF THE INVENTION

1. Field Of The Invention

The present invention relates to the field of medical instrumentation. More particularly, the present invention relates to balloon retention catheter devices for introducing fluids and the like into blood vessels, ducts and other human and animal body cavities and to methods for retaining such devices in a fixed position in the human body.

2. The Prior Art

Catheter devices are in wide use in various medical applications requiring transport of fluids to and from bodily vessels, ducts and cavities. In many catheter applications, such as various radiological applications, it is important to establish the position of the tip of the catheter at a specified location in the body and maintain that position during the performance of the medical procedure during which the catheter is used.

Catheters incorporating one or more inflatable balloons as retention devices are known in the prior art. Because of the ability of such a catheter to be retained in a fixed position once it is put into place in a body vessel or other passage and the balloon or balloons inflated, such catheter devices have found numerous medical applications.

Balloon retention catheters usually comprise a length of flexible tube having a diameter suitable for a particular application. The tubing includes a first lumen for passage of a fluid therethrough. The devices further include one or more inflatable balloons circumferentially disposed around the outer wall of the catheter. In some prior art devices, each balloon communicates with its own lumen terminating in an aperture through which a fluid, usually air, may be introduced to inflate the balloon after the catheter has been put in place at a desired position in a blood vessel, bile duct, or other body cavity. In other prior art devices, both balloons communicate with a common lumen terminating in an aperture through which the inflating fluid may be introduced.

There are numerous examples of prior art retention-type catheter devices. U.S. Pat. No. 2,642,874 to Keeling discloses a catheter including two balloons communicating with a first common inflation lumen and a second lumen terminating at the surface of the circumference of the catheter wall between the two balloons. Keeling teaches insertion of the catheter into the penis to deliver medication to a selected site along the path of the urethra or to remove fluid from a selected region in the urethra by application of a vacuum.

U.S. Pat. No. 2,704,541 to Wyatt discloses a proctoscope which may be immobilized at a selected position in the bowel by an externally applied vacuum communicating with a pair of opposing circumferentially disposed suction plates. The Wyatt device does not employ balloons and relies solely on the suction plates for retention.

U.S. Pat. No. 3,096,764 to Uddenberg discloses a device for retention of a cervix during medical procedures. The Uddenberg device comprises a suction cup having a mouth for enveloping and retaining a cervix.

U.S. Pat. No. 3,438,375 to Ericson discloses a retention catheter for drainage of body fluids. The Ericson device includes a single inflatable balloon located near the tip of the device and positioned relative to a drainage opening in a drainage lumen such that, when inflated, the balloon prevents the body cavity walls from entering the drainage opening.

U.S. Pat. No. 4,022,216 to Stevens discloses a urological catheter for insertion into a patient's bladder. A first balloon, located at the catheter tip, acts as a cushion to prevent the catheter tip from injuring the bladder wall. A second circumferentially disposed inflatable balloon acts as a retention device. A drainage opening is located between the two balloons.

U.S. Pat. No. 4,180,076 to Betancourt discloses a nasogastric catheter. The Betancourt device includes two separately inflatable balloons. Betancourt teaches inflating one or both balloons depending on one of the numerous disclosed purposes to which the catheter is being put.

U.S. Pat. No. 4,423,725 to Baran et al. discloses a surgical cuff. The Baran et al. device includes three circumferentially disposed inflatable cuffs or balloons. The center balloon is double walled and the outer wall is perforated, allowing introduction of anesthetic to the region of body tissue surrounding the cuff.

BRIEF DESCRIPTION OF THE INVENTION

According to a first aspect of the present invention, a retention catheter comprises a length of flexible tubing having first and second ends, including first, second, and third lumens running therethrough. First and second inflatable balloons are circumferentially disposed about the outside of the tubing located proximate to a first end thereof.

The first lumen includes first and second apertures located proximately to the first and second ends of said tubing, and is adapted to conduct fluid therethrough to or from a body cavity or vessel through the catheter.

The first and second balloons are preferably separated by a small distance, and communicate with the second lumen disposed in the tubing. The end of the second lumen opposite to the balloons is adapted to be connected to means for inflating the balloons.

The third lumen through the tubing terminates at a first end in a first aperture located on the outer wall of the tubing between the first and second balloons and at a second end in a vacuum aperture located proximate to the second end of the tubing opposite to the balloon end. The end of the third lumen opposite to the balloons is adapted to be connected to means for pulling a vacuum.

According to the present invention, the catheter is inserted in a body cavity and the balloons are inflated to a desired degree by forcing a fluid, such as water or air through the second lumen commonly connected to the balloons. A vacuum is then drawn through the third lumen, thus pulling in the walls of the body cavity in the region between the two balloons. The dual action of the inflated balloons and the vacuum results in an improved retention of the catheter device. Medication, dyes, gasses, contrast materials, or the like may be introduced, or body fluids withdrawn through the first lumen.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

Figure 1:
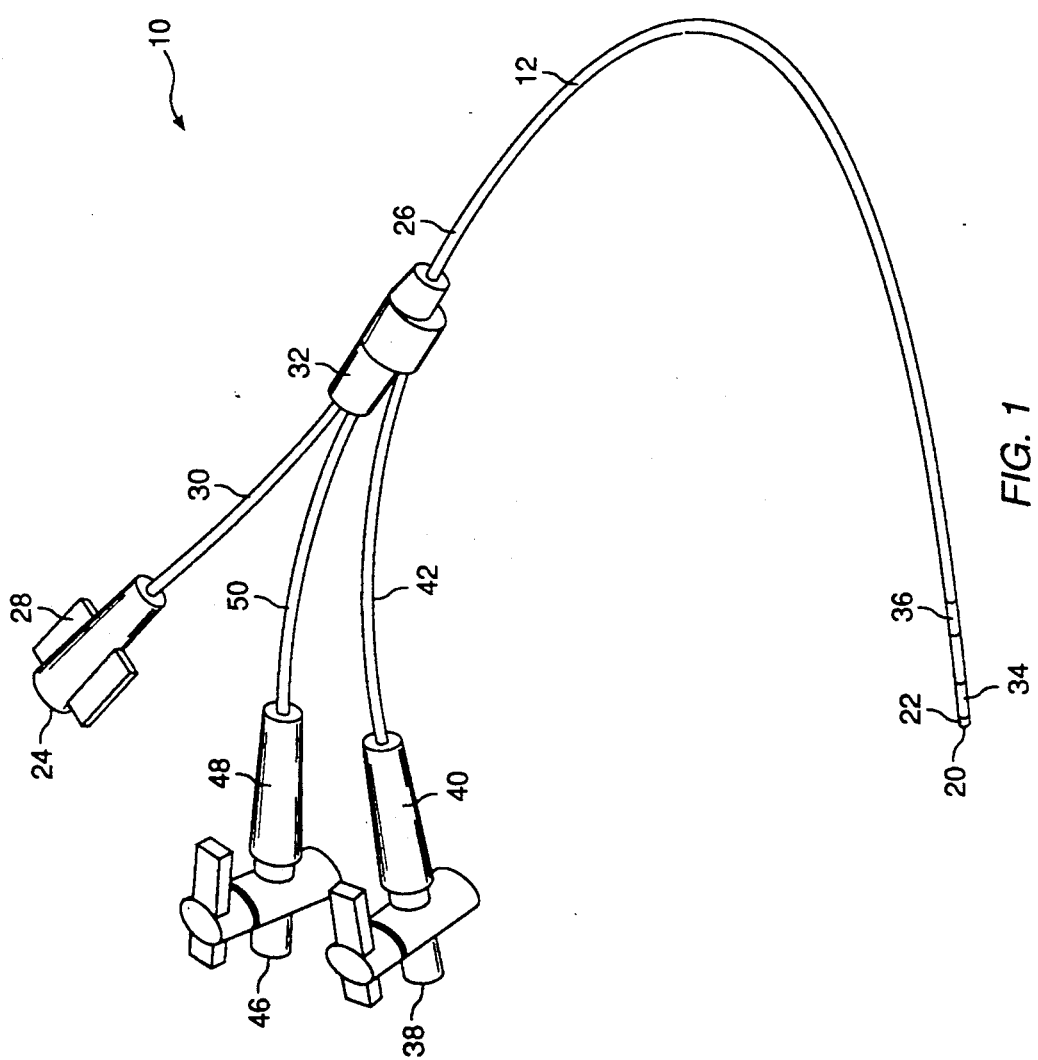
FIG. 1 is a perspective view of a retention catheter according to a presently preferred embodiment of the invention.
Figure 2:
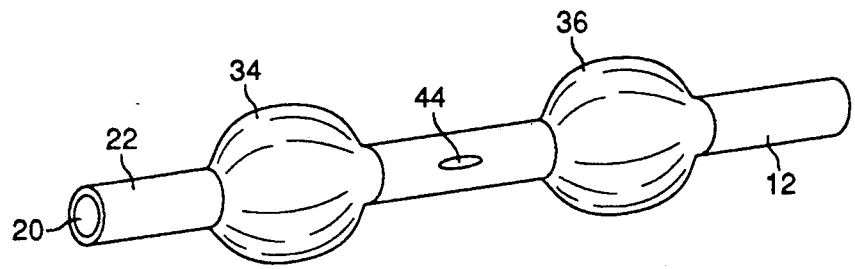
FIG. 2 is a perspective view of a portion of the retention catheter of FIG. 1 showing the balloons in their inflated position.
Figure 4:
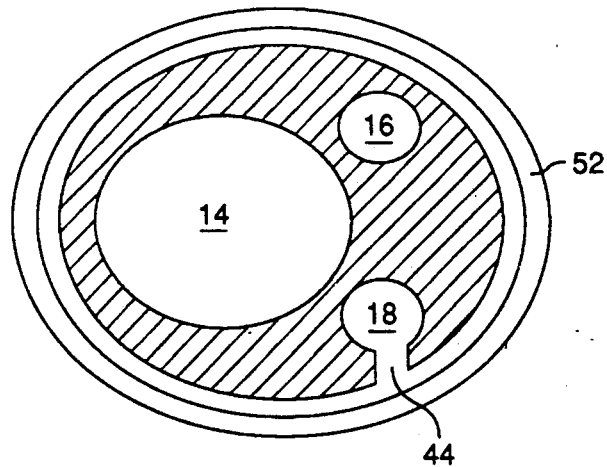
FIG. 4 is a cross sectional view of the catheter of the present invention take through lines 4—4 of FIG. 3.

Referring first to FIGS. 1, 2 and 4, a retention catheter 10 according to the present invention comprises a length of flexible tubing 12. Tubing 12 may be formed from various materials as is well known in the art. Suitable materials include, but are not limited to thermoplastics, polyvinylchloride, soft nylon, latex, and thermoplastic elastomers. Also included are polyethylenes (both high and low density), polypropylenes, ionomers, polyesters and polyurethanes.

Flexible tubing 12 includes first, second, and third axially disposed collinear passageways or lumens 14, 16, and 18, respectively, disposed therein. In a presently preferred embodiment of the invention, first, second, and third lumens 14, 16, and 18 are formed into catheter 10 by extrusion of the catheter tube material as shown in cross section in FIG. 4, although other fabrication means may be employed. FIG. 4 illustrates one embodiment of the present invention where multilumens are employed. The lumens can have different geometric configurations and need not possess circular cross sections. Additionally, catheter 10 can be of a co-axial design, with one lumen being formed over another in a sequential manner.

First lumen 14 is used to conduct a fluid through catheter 10 and terminates at a first end in one or more apertures 20 located proximate to a first end 22 of tubing 12, and at a second end in aperture 24 located proximate to a second end 26 of tubing 12. In the embodiment shown in FIG. 1, a fitting 28 attached to tube 12 by a tube 30 terminating in manifold 32, is used as is well known in the art, generally known as a proximal adaptor. 16 A pair of spaced-apart inflatable balloons 34 and 36 are located proximate to first end 22 of tubing 12. Balloons 34 and 36 may be formed from various materials depending upon the use to which catheter 10 is to be put. Suitable balloon materials include but are not limited to polyethylenes ionomers, polyvinylchloride, polyurethanes, and latex. In one embodiment, balloons 34 and 36 may be formed from latex by circumferentially securing latex bands around tubing 22 with a suitable adhesive, as is known in the art. Depending on the material from which the balloons are formed they can be secured to tubing 22 by heat bonding, solvent bonding, adhesive bonding, or RF or ultrasonic bonding.

Figure 3:
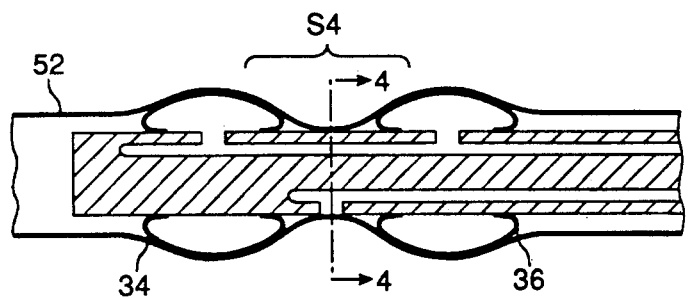
FIG. 3 is a cross sectional axial view of the balloon end of the catheter of FIG. 1 inserted in a vessel, illustrating the balloons in their inflated condition with a vacuum pulled, showing the retention effect of the present invention.

Second lumen 16 is used to inflate balloons 34 and 36 and at its first end communicates with the inside surfaces of balloons 34 and 36 as shown in FIG. 3. At its second end, second lumen 16 terminates in an inflation aperture 38 adapted to be connected to a means for inflating balloons 34 and 36 as is well known in the art.

As shown in FIG. 1, inflation aperture 38 lies at the end of a first valve adaptor 40 at the end of tubing 42 communicating with second lumen 16 in tube 12 through manifold 32. Balloons 34 and 36 are inflated sufficiently to seal the interior of the body cavity wall. They are inflated to size which is slightly larger than the interior cross-sectional area of body cavity 52.

Third lumen 18 is used to pull a vacuum between balloons 34 and 36 when they are inserted in a vessel in order to partially collapse the wall of a vessel or body cavity between balloons 34 and 36 to more securely hold catheter 10 in place during medical 18 procedures with which it is utilized. Third lumen 18 terminates at a first end in one or more apertures 44 located in the outer wall of tubing 10 positioned between balloons 34 and 36 and terminates at a second end proximate to second end 26 of tubing 12 in a vacuum aperture 46 adapted to be connected to a means for pulling a vacuum from the volume defined by the facing surfaces of balloons 34 and 36 and the wall of a vessel o body cavity. As shown in FIG. 1, vacuum aperture 46 lies at the end of a second valve adaptor 48 at the end of tubing 50 communicating with third lumen 18 in tube 12 through manifold 32.

Balloons 34 and 36 are shown in their inflated position in FIG. 3, depicting a catheter 10 according to the present invention inserted into a body cavity 52 after a vacuum has been pulled through third lumen 18 thus partially collapsing the wall of vessel 52 around its entire circumference at region 54 between inflated balloons 28 and 30. Multiple apertures 44 can be employed in order to effect the best collapse of the body cavity 52.

According to a presently preferred embodiment of the invention, a catheter as disclosed herein is first inserted into a body cavity or vessel. Balloons 34 and 36 are next inflated as is known in the art by directing a fluid, such as air or water through second lumen 18. Next, a vacuum is pulled in the volume defined inside the wall of vessel or body cavity 52 between balloons 34 and 36. The pressure differential across the walls of vessel or body cavity 52 forces the wall to assume the contour of the catheter with inflated balloons, assuring a secure positioning of catheter 10 within vessel or body cavity 52.

The present invention is suitable for a variety of different applications and may be used in vessels, ducts, arteries, veins, various tracts including but not limited to the intestinal and urinary tracts, as well as the urethra. The words "cavity" or "vessel" used herein should be understood by those of ordinary skill in the art to refer to all such body features. Those of ordinary skill in the art will recognize that individual catheters described herein according the present invention will be appropriately sized depending on the particular application for which they will be used.

Use of the method according to the present invention provides a very effective way to increase the amount of tissue or other body material which comes into contact with a catheter when body cavity 52 is caused to collapse between balloons 34 and 36. This increases the amount of friction between the tissue and catheter 10 in order to restrict the movement and motion of catheter 10. The greatest amount of friction is achieved when the body tissue follows the exact contour of the exterior of catheter 10 with balloons 34 and 36 inflated in region 54 of body cavity 52. Balloons 34 and 36 provide a substantially airtight seal between the tissue and catheter 10 which allows aperture 44 to draw the tissue to the exterior surface of body cavity 52. As previously mentioned, a plurality of apertures 44 may be utilized to draw in the tissue in the region between balloons 34 and 36.

EXAMPLE 1

Cholanoioqram

The present invention is used in a diagnostic procedure to determine if there are any stones in the cystic duct. An incision is made in the cystic duct, catheter 10 is inserted into the duct, balloons 34 and 36 are inflated, and a vacuum is drawn through third lumen 18. Once catheter 10 has been secured as described, a suitable dye is inserted into the duct in a forward direction. Catheter 10 is prevented from moving from a position in the cystic duct and the risk of catheter 10 "popping out" is greatly reduced.

EXAMPLE 2

Coronary Guiding Catheter

Catheter 10 is used as a "channel tube" which serves as a guide for a coronary dilation catheter according to the method of the present invention. Catheter 10 may include a hook which becomes seated in the aortic tract. Catheter 10 is disposed in a tract, balloons 34 and 36 are inflated, and a vacuum is drawn through third lumen 18, thus securing catheter 10 in place. A dilator catheter is then inserted through catheter 10 and is at least partially positioned into a coronary artery to dilate the vessel.

EXAMPLE 3

Angiographic Catheter

An angiographic catheter is used to inject dye into a coronary artery according to the method of the present invention. Catheter 10 is used as an angiographic catheter and provides a stable positioning mechanism in the coronary vessel so that catheter 10 is in a fixed position so that dye can be injected while catheter 10 is so fixed. Catheter 10 is disposed in a coronary artery, balloons 34 and 36 are inflated, and a vacuum is drawn through third lumen 18, thus securing catheter 10 in place in contact with the inner artery wall.

EXAMPLE 4

Gynecology

The present invention is employed for gynecological uses for hysterosalpingography, salpingoplasties, hydrotubation, Rubin's Test, various laparoscopic procedures, tubal sterilizations, fertility studies and minilaps. Tubal catheters have a variety of functions in gynecological procedures. In such procedures as hysterosalpingography and alternative salpingoplasties the catheter will be used to both support the fallopian tube and carry injection dye to view the tube for any and all obstructions or adhesions. In these procedures, a tubal catheter is used much like an angeographic catheter but in the fallopian tubes. Also, tubal catheters are put into the fallopian tube during and after surgery to inject Ringer's lactate and other cleansing and sterilizing solutions.

EXAMPLE 6

Urology

A urological catheter is used in conjunction with a laser fiber to break up and remove stones in the urethra between the kidneys and bladder. The method of the present invention provides a stable positioning mechanism in the urethra so that catheter 10 is in a fixed position so that the stone may be located and broken up by fiber optic procedures while catheter 10 is so fixed. Catheter 10 is inserted into and disposed in the urethra, and the stone is located using an optical fiber or fiber bundle disposed within the third lumen. Balloons 34 and 36 are inflated, and a vacuum is drawn through third lumen 18, thus securing catheter 10 in place in contact with the inner wall of the urethra. Laser energy is then delivered to the site of the stone through the optical fiber or fiber bundle disposed within the third lumen.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A method for securing a catheter in a body vessel, said catheter comprising a length of flexible tubing having first and second ends, said tubing including a plurality of axial lumens running therethrough, said tubing further including first and second inflatable balloons circumferentially disposed about the outside of said tubing located proximate to said first end thereof, said first and second balloons separated by a selected distance and communicating with at least one of said plurality of lumens, at least one of said plurality of lumens terminating in a first aperture located on the outer wall of said tubing between said first and second balloons, said method including the steps of:

inserting said catheter into a body vessel;
   inflating said balloons;
   pulling a vacuum in a volume defined between said balloons and inside a wall defining said body vessel; and
   partially collapsing said wall of said body vessel between said balloons in said volume to more securely position said catheter in said body vessel.

2. The method of claim 1 wherein said body vessel is chosen from the group including arteries, veins, bile ducts, esophagus, fallopian tubes, urethra, and intestines.

3. A method for securing a catheter in a body vessel, said catheter comprising a length of flexible tubing having first and second ends, said tubing including first and second axial lumens running therethrough, first and second inflatable balloons circumferentially disposed about the outside of said tubing located proximate to said first end thereof, said first and second balloons separated by a selected distance and communicating with said first lumen, said second lumen terminating in a first aperture located on the outer wall of said tubing between said first and second balloons, said method including the steps of:

inserting said catheter into a body vessel;
   inflating said balloons;
   pulling a vacuum in a volume defined between said balloons and inside a wall defining said body vessel; and
   partially collapsing a wall of said body vessel between said balloons in said volume to more securely position said catheter in said vessel.

4. The method of claim 3 wherein said body vessel is chosen from the group including arteries, veins, bile ducts, esophagus, fallopian tubes, urethra, and intestines.

5. A method for positionally securing a catheter in a body vessel and for delivering a fluid therethrough into said body vessel, said catheter comprising a length of flexible tubing having first and second ends, said tubing including first, second and third axial lumens running therethrough, first and second inflatable balloons circumferentially disposed about the outside of said tubing located proximate to said first end thereof, said first and second balloons separated by a selected distance and communicating with said first lumen, said second lumen terminating in a first aperture located on the outer wall of said tubing between said first and second balloons, and said third lumen terminating in apertures generally located near proximate and distal ends of said tubing, said method including the steps of:
- inserting said catheter into a body vessel;
- inflating said balloons;
- pulling a vacuum in the volume defined between said balloons and inside a wall defining said vessel; and
- delivering said fluid into said body vessel through said third lumen.

6. The method of claim 5 wherein said body vessel is chosen from the group including arteries, veins, bile ducts, esophagus, fallopian tubes, urethra, and intestines.

7. A method for securing a catheter in a body vessel and for delivering a fluid therethrough into said body vessel, said catheter comprising a length of flexible tubing having first and second ends, said tubing including a plurality of axial lumens running therethrough, said tubing further including first and second inflatable balloons circumferentially disposed about the outside of said tubing located proximate to said first end thereof, said first and second balloons separated by a selected distance and communicating with at least a first one of said plurality of lumens, a second one of said plurality of lumens terminating in a first aperture located on the outer wall of said tubing between said first and second balloons, and a third of said plurality of lumens terminating in apertures generally located near proximate and distal ends of said tubing, said method including the steps of:
- inserting said catheter into a body vessel;
- inflating said balloons; and
- pulling a vacuum in the volume defined between said balloons and inside a wall defining said body vessel through said second lumen, and
- delivering said fluid into said body vessel through said third lumen.

8. The method of claim 7 wherein said body vessel is chosen from the group including arteries, veins, bile ducts, esophagus, fallopian tubes, urethra, and intestines.

* * * * *

UNITED STATES PATENT AND TRADEMARK OFFICE
CERTIFICATE OF CORRECTION

PATENT NO. : 5,188,595
DATED : February 23, 1993
INVENTOR(S) : Jacobi, Roger P.

It is certified that error appears in the above-identified patent and that said Letters Patent is hereby corrected as shown below:

- Delete "6" in column 5, line 61

- Replace with "5" to Read "Example 5"

Signed and Sealed this

Twenty-eighth Day of December, 1993

*Attest:*

BRUCE LEHMAN

*Attesting Officer*    Commissioner of Patents and Trademarks